United States Patent
Morey et al.

(10) Patent No.: US 11,446,059 B2
(45) Date of Patent: Sep. 20, 2022

(54) IMPLANT INSERTION DEVICE

(71) Applicant: Boston Scientific Limited, Hamilton (BM)

(72) Inventors: Subodh Morey, Ponda (IN); Rajivkumar Singh, Thane (IN); Sumit Malik, Gurgaon (IN); Rohit Bhardwaj, Kurukshetra (IN); Junaid Mohammed Shaikh, Surat (IN); Siddharth Mishra, Churu (IN); Sushil Nagpal, Haryana (IN); Sushil Kumar, Bihar (IN); Amit Chaudhary, Uttar Pradesh (IN); Arun Adhikarath Balan, Kerala (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 534 days.

(21) Appl. No.: 16/597,301

(22) Filed: Oct. 9, 2019

(65) Prior Publication Data
US 2020/0113599 A1    Apr. 16, 2020

Related U.S. Application Data

(60) Provisional application No. 62/745,857, filed on Oct. 15, 2018.

(51) Int. Cl.
| | | |
|---|---|---|
| *A61B 17/34* | (2006.01) | |
| *A61B 17/00* | (2006.01) | |
| *A61F 2/26* | (2006.01) | |

(52) U.S. Cl.
CPC ............ *A61B 17/3468* (2013.01); *A61F 2/26* (2013.01); *A61B 2017/00407* (2013.01); *A61B 2017/00424* (2013.01)

(58) Field of Classification Search
CPC .... A61B 2017/291; A61B 2017/00424; A61B 2017/00407; A61B 17/3468; A61B 17/2909; A61F 2/26
See application file for complete search history.

(56) References Cited

U.S. PATENT DOCUMENTS

| | | | |
|---|---|---|---|
| 4,244,370 A | 1/1981 | Furlow et al. | |
| 5,281,197 A * | 1/1994 | Arias ................ | A61M 37/0069 604/209 |

(Continued)

FOREIGN PATENT DOCUMENTS

| | | |
|---|---|---|
| WO | 2007134005 A1 | 11/2007 |
| WO | 2010065274 A1 | 6/2010 |
| WO | 2019183190 A1 | 9/2019 |

OTHER PUBLICATIONS

International Search Report and Written Opinion for Application No. PCT/US2019/055659, dated Jan. 16, 2020, 16 pages.

*Primary Examiner* — Majid Jamialahmadi
(74) *Attorney, Agent, or Firm* — Brake Hughes Bellermann LLP

(57) ABSTRACT

According to a general aspect, an insertion device includes an elongate member defining a lumen, a handle member movably coupled to the elongate member, a plunger member, at least a portion of the plunger member being disposed within the lumen defined by the elongate member, and an actuation member operatively coupled to the plunger member, the plunger member being configured to move from a first position within the lumen to a second location within the lumen in response to the actuation member being actuated.

11 Claims, 13 Drawing Sheets

(56) References Cited

U.S. PATENT DOCUMENTS

| | | | |
|---|---|---|---|
| 5,868,729 | A | 2/1999 | Pelfrey et al. |
| 7,066,878 | B2 | 6/2006 | Eid |
| 2006/0195097 | A1 | 8/2006 | Evans et al. |
| 2017/0105657 | A1 | 4/2017 | Eid |

* cited by examiner

IMPLANT INSERTION DEVICE

CROSS-REFERENCE TO RELATED APPLICATION

This application is a Nonprovisional of, and claims priority to, U.S. Patent Application No. 62/745,857, filed on Oct. 15, 2018, entitled "IMPLANT INSERTION DEVICE", which is incorporated by reference herein in its entirety.

TECHNICAL FIELD

This disclosure relates generally to devices for insertion of bodily implants and, more specifically, to insertion devices for bodily implants, such as penile prostheses.

BACKGROUND

One treatment for chronic, organic, male erectile dysfunction is the implantation of a penile prosthesis that mechanically erects the penis. Such prostheses can have different physical constructions (e.g., materials, mechanical structure and function, etc.) and configurations (e.g., physical dimensions, etc.). For instance, such a penile prosthesis can be in the form of a cylinder (e.g., malleable, inflatable, etc.) that is selected based on the physical requirements of an intended recipient (a patient). For instance, an appropriate penile prosthesis can be implanted within a corpus cavernosum (corpus cavernosa) of a patient's penis by medical personnel that are trained and knowledgeable regarding the implantation and use of penile prostheses.

Insertion devices (e.g., furlow insertion devices) can be used to facilitate the insertion of a penile prosthesis into the corpus cavernosum of a patient. Such furlow insertion devices can be used for measurement of an insertion length within the corpus cavernosum, as well as for facilitating insertion of a penile prosthesis by deploying a suture-carrying needle, where the needle and/or suture are used to introduce (draw, pull, insert, implant, etc.) the prosthesis into the corpus cavernosum.

In some existing devices, a needle (e.g., which can be referred to as a Keith needle) used in the insertion of a penile prosthesis can be deployed from an insertion device that may be used and more than one surgical procedure. Such insertion devices often require cleaning and sterilization before being used on a second or subsequent patient. Also, in some existing devices, a handle portion of the insertion device is fixedly coupled to an elongate portion of the insertion device.

Accordingly, in some instances it may be desirable to provide a single use insertion device. Additionally, in some instances it may be desirable to provide an insertion device that includes a handle portion that is movable or adjustable with respect to the elongate portion.

SUMMARY

According to a general aspect, an insertion device includes an elongate member defining a lumen, a handle member movably coupled to the elongate member, a plunger member, at least a portion of the plunger member being disposed within the lumen defined by the elongate member, and an actuation member operatively coupled to the plunger member, the plunger member being configured to move from a first position within the lumen to a second location within the lumen in response to the actuation member being actuated.

In some embodiments, the handle member is rotatably coupled to the elongate member. In some embodiments, the handle member is pivotally coupled to the elongate member.

In some embodiments, the insertion device includes a ratchet member, the ratchet member having a first portion coupled to the elongate member and a second portion coupled to the handle member. In some embodiments, the first portion of the ratchet member configured to move with respect to the second portion of the ratchet member.

In some embodiments, the first portion of the ratchet member has a plurality of teeth members, the second portion of the ratchet member has a plurality of teeth members, the plurality of teeth members of the first portion of the ratchet member being configured to engage the plurality of teeth members of the second portion of the ratchet member. In some embodiments, the ratchet member is configured to help retain the handle member in a first position with respect to the elongate member.

In some embodiments, the ratchet member is configured to help retain the handle member in a first position with respect to the elongate member, the ratchet member being configured to help retain the handle member in a second position with respect to the elongate member, the first position being different than the second position.

In some embodiments, the actuation member is movably coupled to the handle member. In some embodiments, the actuation member is slideably coupled to the handle member. In some embodiments, the actuation member includes an extension member that extends from an outer surface of the handle member.

In some embodiments, the plunger is configured to engage a needle and move the needle from a first location within the lumen defined by the elongate member to a second location within the lumen defined by the elongate member. In some embodiments, the plunger is configured to engage a needle and move the needle from a location within the lumen defined by the elongate member to a location outside of the lumen defined by the elongate member.

In some embodiments, the elongate member includes a sidewall that defines the lumen, the sidewall includes a slot that extends along at least a portion of the length of the elongate member. In some embodiments, the elongate member incudes a plurality of markings along the length of the elongate member.

According to another aspect, a medical device includes an insertion device, having, an elongate member defining a lumen; a handle member movably coupled to the elongate member; a plunger member, at least a portion of the plunger member being disposed within the lumen defined by the elongate member; and an actuation member operatively coupled to the plunger member, the plunger member being configured to move from a first position within the lumen to a second location within the lumen in response to the actuation member being actuated; an implant, having an inflation member; and a needle, the needle coupled to the inflation member, the needle configured to be disposed at least partially within the lumen defined by the elongate member.

In some embodiments, the handle member is rotatably coupled to the elongate member. In some embodiments, the handle member is pivotally coupled to the elongate member.

In some embodiments, the medical device includes a ratchet member, the ratchet member having a first portion coupled to the elongate member and a second portion coupled to the handle member. In some embodiments, the first portion of the ratchet member configured to move with respect to the second portion of the ratchet member.

DETAILED DESCRIPTION

Figure 1:
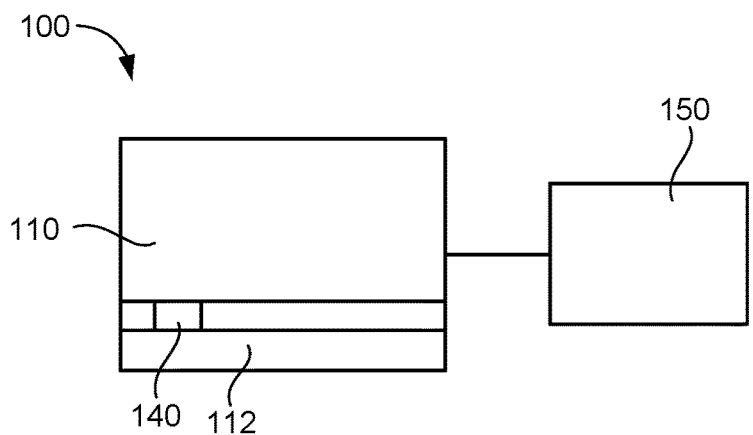
FIG. 1 is a schematic illustration of an insertion device according to an embodiment.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as insertion devices for penile prostheses or other bodily implants. The term patient may hereafter be used for a person who benefits from the medical device or the methods disclosed in the present disclosure. For example, the patient can be a person whose body is implanted using the medical device or benefits from the methods disclosed for operating the medical devices of the present disclosure. For example, in some embodiments, the patient may be a human male, a human female, or any other mammal.

The terms proximal and distal described in relation to various devices, apparatuses, and components as discussed in the subsequent text of the present disclosure are referred to using a point of reference. The point of reference, as used in this description, is a perspective of a person who uses the disclosed insertion devices to implant a bodily implant, such as a penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther from, or farthest from the person.

The embodiments discussed herein may provide improvements to penile prosthesis insertion devices (e.g., furlow insertion devices, furlow insertion tools, insertion tools, devices, tools, etc.). For example, such insertion devices can be configured to self-load and secure a needle in a barrel or lumen of the insertion device, which can prevent premature deployment of the needle (e.g., prevent the needle from inadvertently coming out of the tool).

Further, in some embodiments, such insertion devices can be produced using low-cost bio-compatible materials, such as bio-compatible plastics, or otherwise, as compared with tools constructed using primarily surgical grade metals, for example. Accordingly, in certain embodiments, an insertion device such, as those described herein, can be used for a single surgical procedure. For example, in some cases the insertion devices may be used for a single surgical procedure and then disposed of.

In some embodiments, an insertion device can be ergonomically arranged to facilitate easier access to an implantation site (e.g., incision site) for some patients, such as heavy-set patients by allowing for manipulation of the device at a distance that is farther away from the patient's body than in some current insertion devices. Additionally, in some embodiments, the insertion device may be arranged such that during the procedure, the hands of the physician are disposed away or spaced from the skin of the patient. Also, in certain embodiments, an insertion device may include a handle portion that is movably coupled to an elongate portion of the insertion device.

FIG. 1 schematically illustrates an insertion device 100, such as a furlow insertion device. In some cases, the insertion device may be used for insertion (implantation, etc.) of a penile prosthesis in a penis of a patient according to an embodiment. In other cases, the insertion device may be used to insert a different type of bodily implant into a body of a patient.

As illustrated in FIG. 1, the insertion device 100 includes an elongate member or portion 110 and a handle member or portion 150. In some embodiments, the handle portion 150 is movably coupled to the elongate portion 110. For example, in some embodiments, the handle portion 150 is rotatably or pivotally coupled to the elongate portion 110. In other embodiments, the handle portion 150 is slideably or otherwise moveably coupled to the elongate portion 110. In other embodiments, the handle portion 150 is fixedly coupled to the elongate portion 110.

The elongate portion 110 defines a lumen 112. In some embodiments, the elongate portion 110 includes a sidewall or sidewall member that defines the lumen 112. In some embodiments, the lumen 112 extends along or parallel to at least a portion of a longitudinal axis of the elongate portion 110.

In the illustrated embodiment, the insertion device 100 includes a plunger 140. The plunger 140 is configured to be disposed within and move within the lumen 112. As will be described in more detail below, in some cases the plunger 140 is configured to move from a first location within the lumen 112 to a second location within the lumen 112. In some cases, the plunger 140 is configured to engage a needle (such as a Keith needle) to move the needle within the lumen or to force the needle from a location within the lumen 112 to a location outside of the lumen 112.

In some embodiments, the insertion device 100 includes an actuator. The actuator may be operatively coupled to the plunger 140. Manipulation or actuation of the actuator can cause the plunger 140 to move within the lumen 112.

In some cases, the needle (e.g., a Keith needle), a suture and the penile prosthesis (or other bodily implant) can be used in conjunction with the device 100, or other insertion devices, such as those disclosed herein, for implanting the penile prosthesis (or other bodily implant) into a body of a patient.

For example, in some cases a penile prosthesis may be inserted into a body of the patient using the insertion device 100. Specifically, a cylindrical (e.g., inflatable, malleable, etc.) penile prosthesis can be implanted (inserted, etc.) in a corpus cavernosum of a patient. A method of insertion can include making a penoscrotal or an infrapubic incision in a body of a patient, wherein the incision is located such that a corpus cavernosum of the patient's penis is accessible through the incision. In some cases, an appropriate penile prosthesis can be selected. The selected prosthesis can be attached (coupled with, affixed to, etc.) the suture. The suture can be threaded into (inserted through) an eye of a needle, such as the Keith needle. The needle can then be inserted into the lumen 112 of the elongate member 110.

The method includes manipulating the insertion device 100, via the handle 150, to perform a first insertion of the elongate member or portion 110 of the insertion device 100 into the corpus cavernosum, the insertion of the elongate member 110 being made via the incision. The needle can then be expelled from the lumen 112 using the plunger 140 (such as by manipulating the actuation member to move the plunger 140 and also move the needle within the lumen 112 or to a location outside of the lumen 112). In some cases, the actuation of the plunger causes the needle to, at least partially, exit the patient's body via a glans of the patient's penis. The elongate member 110 can again be removed (withdrawn, etc.) from the corpus cavernosum of the patient, leaving the needle and the suture in place (e.g., with the needle partially extending out of the glans and the suture extending from an eye of the needle within the corpus cavernosum to the penile prosthesis being implanted). The penile prosthesis can be implanted into the corpus cavernosum of the patient by drawing the prosthesis through the incision and into to the corpus cavernosum by pulling the needle and the suture through (out of, etc.) the glans of the patient's penis.

After completing implantation of the penile prosthesis, the insertion tool 100 can disposed of.

Figure 2:
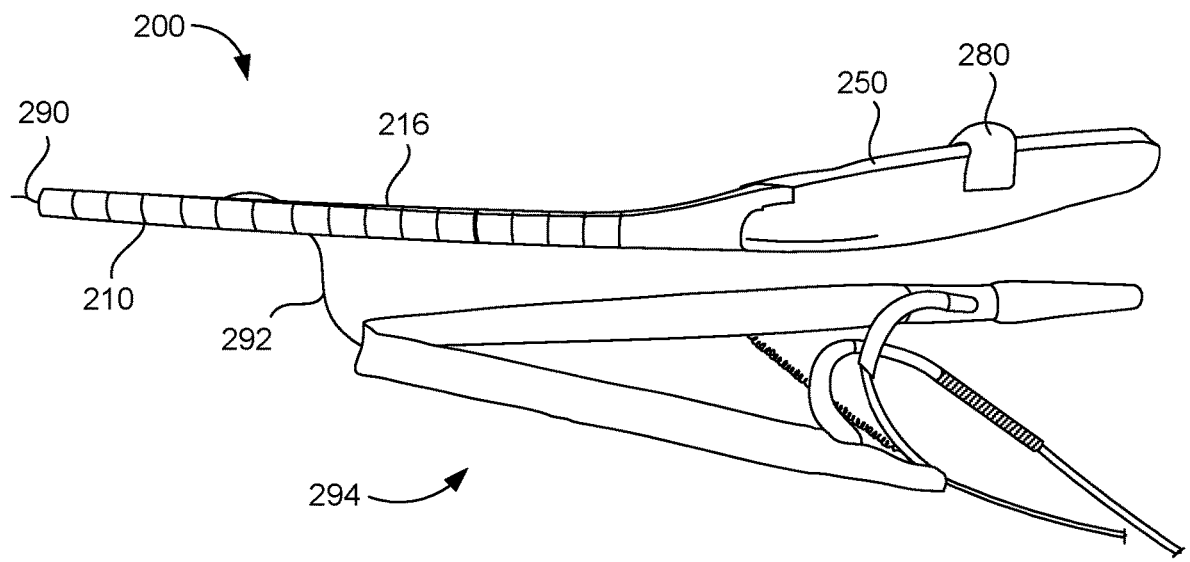
FIG. 2 is a side view of an insertion device coupled to an implant according to an embodiment.

FIGS. 2-7 illustrate an insertion device 200 according to an embodiment. FIG. 2 illustrates the insertion device 200 coupled to a needle 290, a suture 292, and an implant 294.

Figure 3:
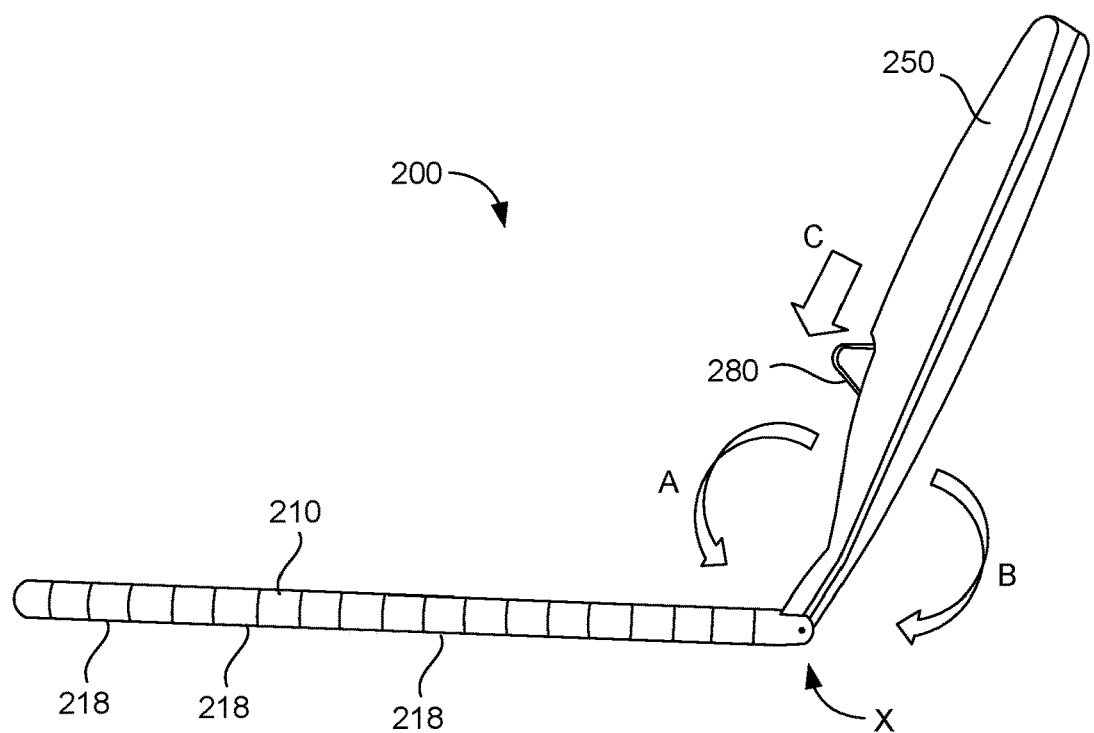
FIG. 3 is a side view of the insertion device of FIG. 2.
Figure 4:
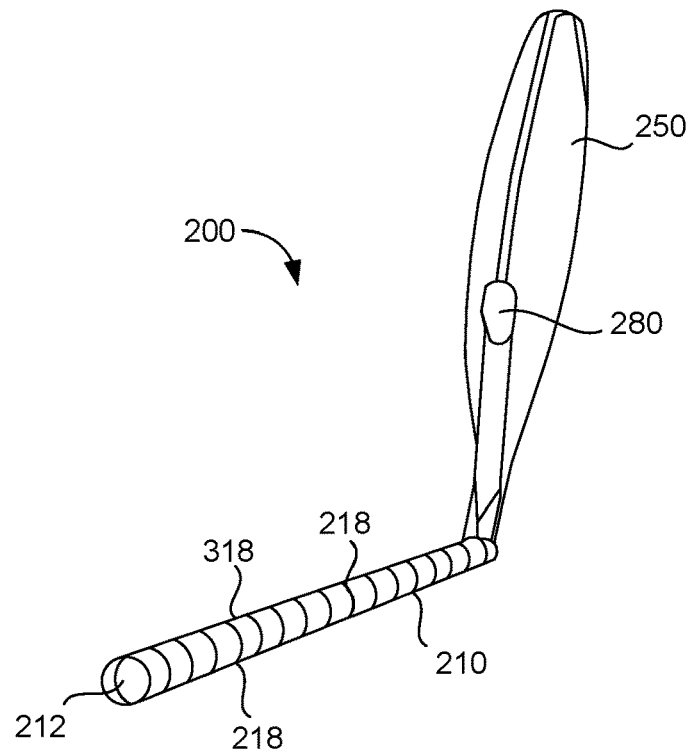
FIGS. 4 and 5 are perspective views of the insertion device of FIG. 2.
Figure 5:
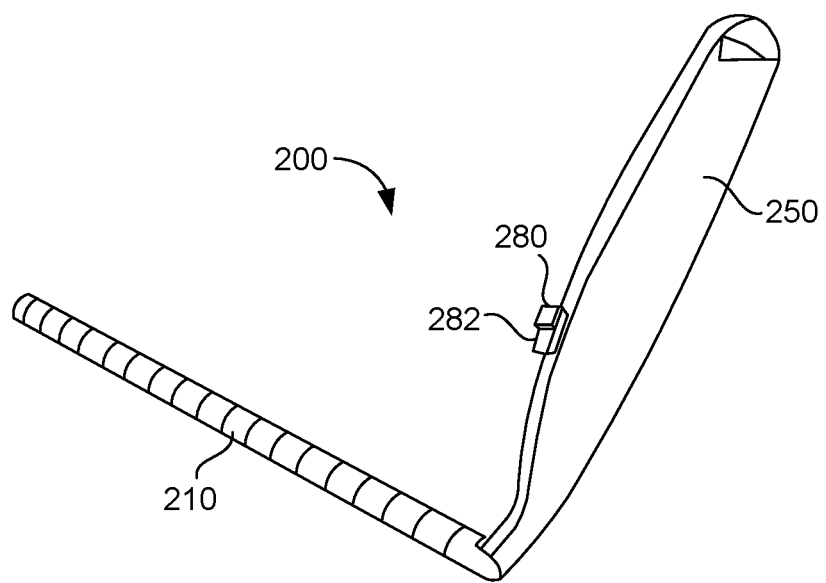
Figure 6:
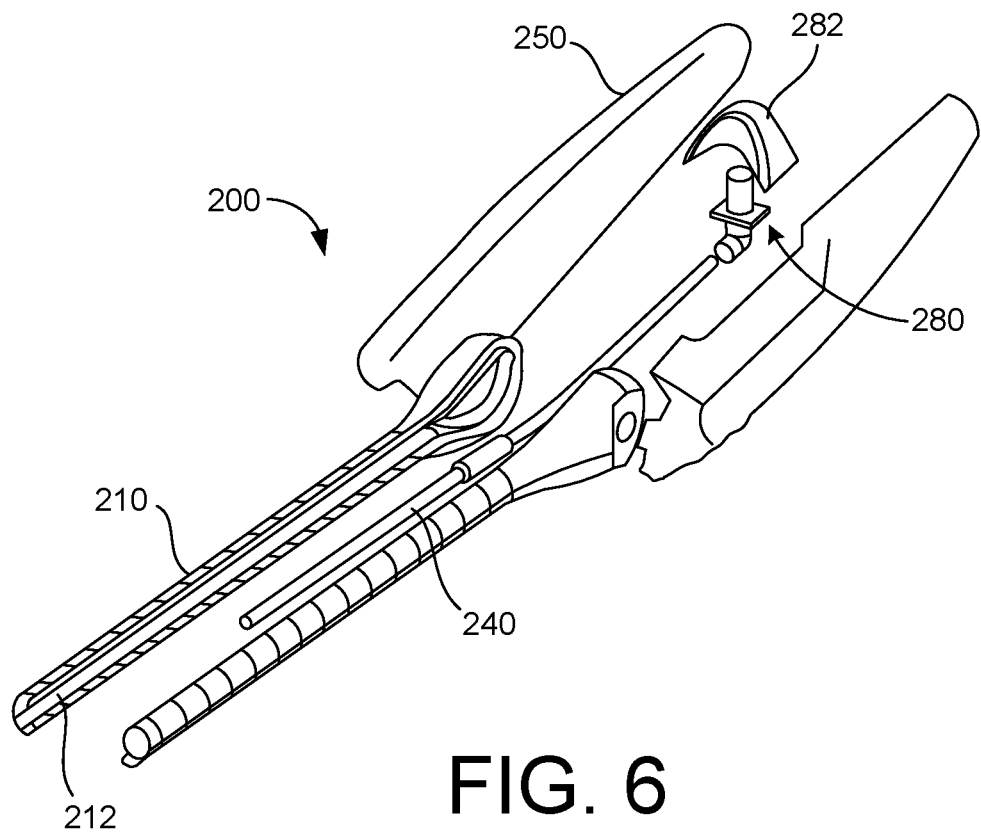
FIG. 6 is an exploded view of the insertion device of FIG. 2.
Figure 7:
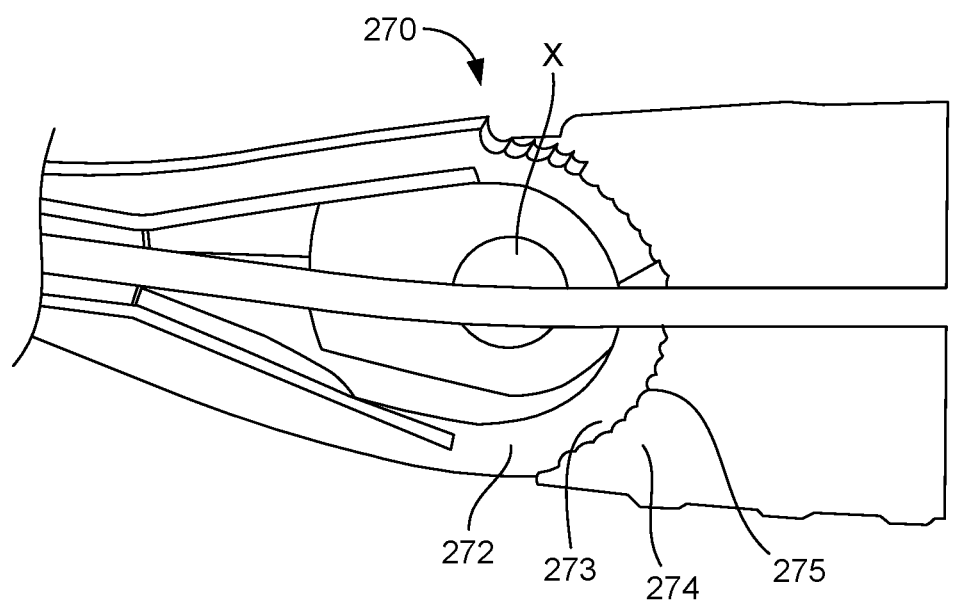
FIG. 7 is a cross-sectional view of a portion of the insertion device of FIG. 2.
Figure 8:
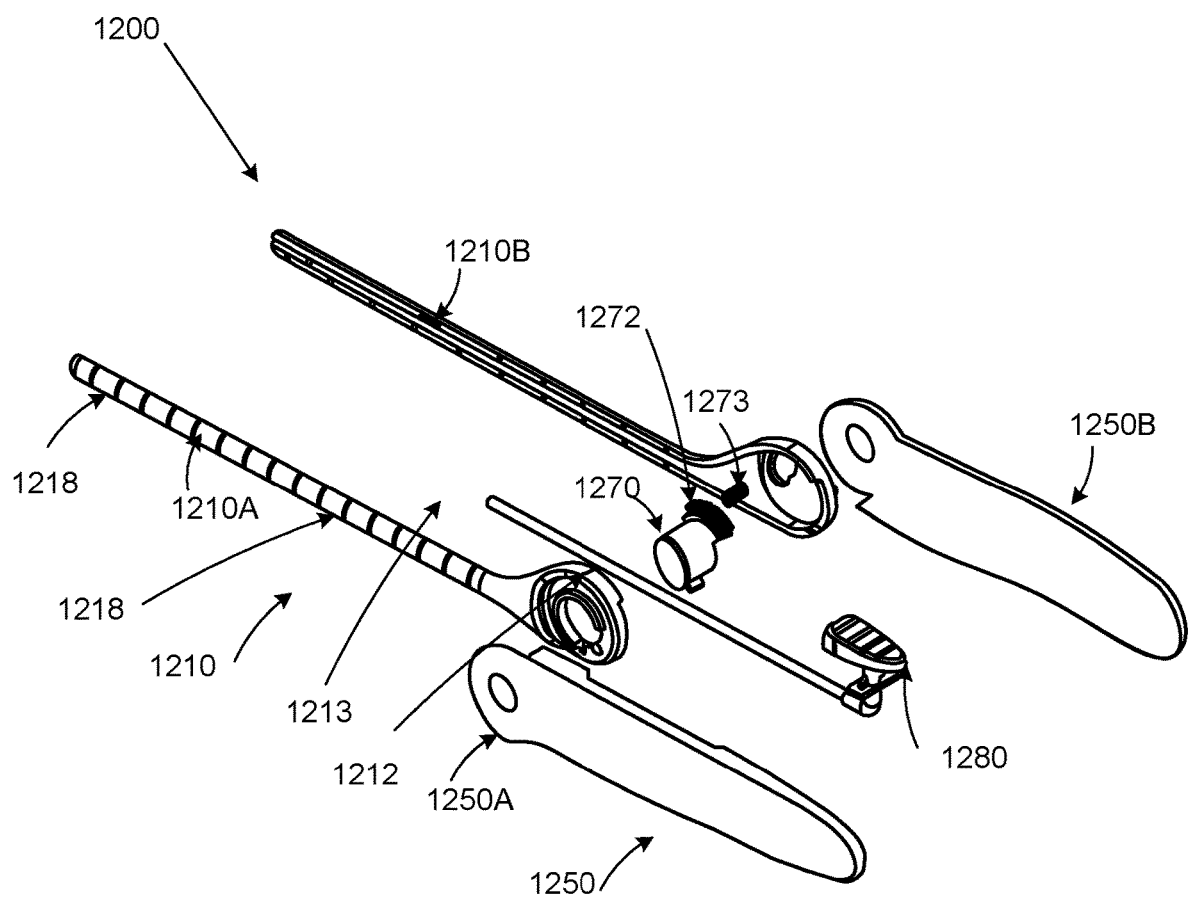
FIG. 8 is an exploded view of an insertion device according to an embodiment.
Figure 9:
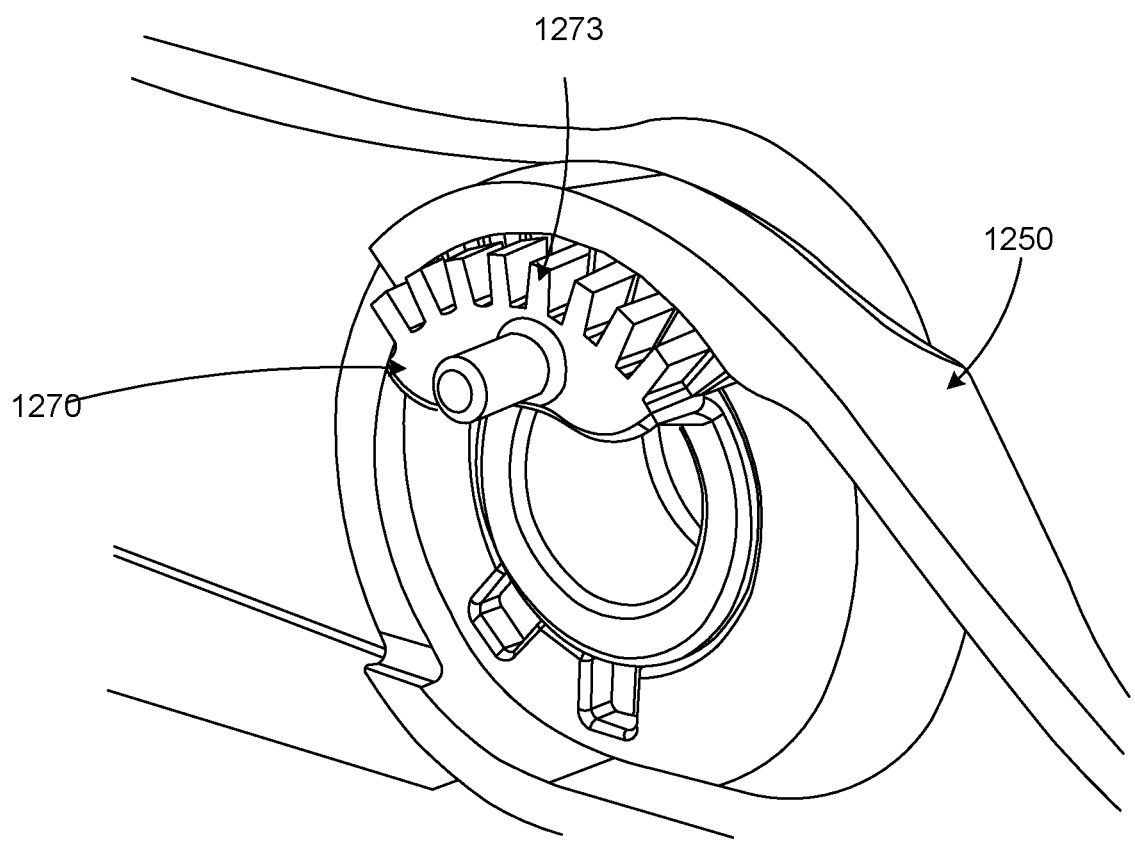
FIG. 9 is a side view of a portion of the insertion device of FIG. 8.
Figure 10:
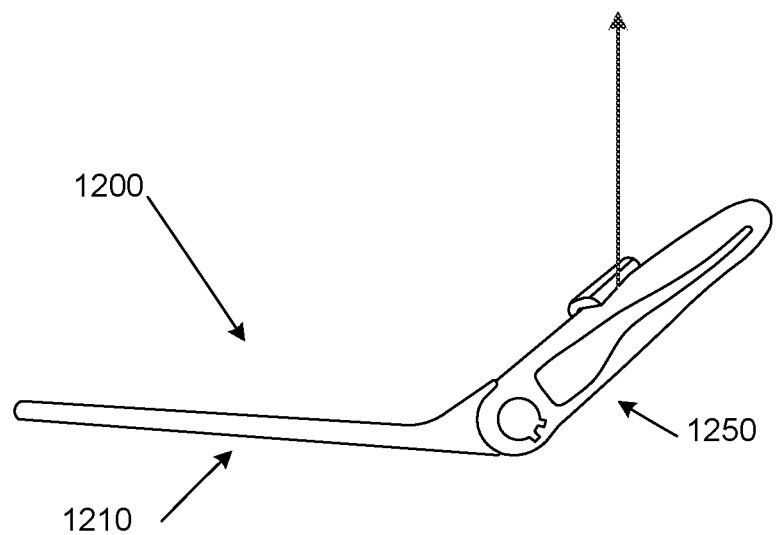
FIG. 10 is a side view of the insertion device of FIG. 8 in a first configuration.
Figure 11:
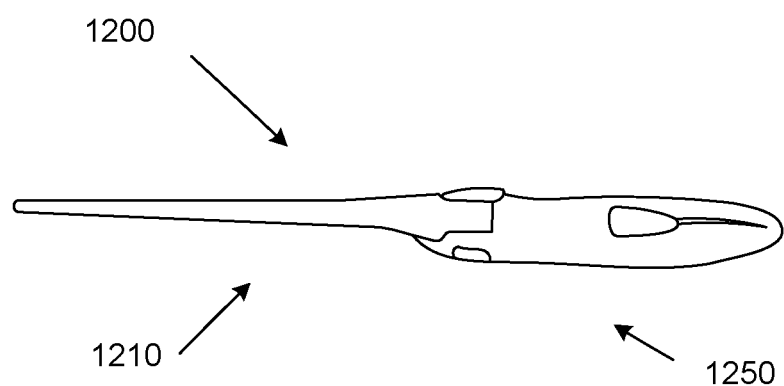
FIG. 11 is a top view of the insertion device of FIG. 8 in a second configuration.

As illustrated the insertion device 200 includes an elongate member or portion 210 and a handle member or portion 250. The handle portion 250 is movably coupled to the elongate portion 210. For example, the handle portion 250 is rotatably or pivotally coupled to the elongate portion 210. As best illustrated in FIGS. 3 and 7, the handle portion 250 may move with respect to the elongate portion 210 in the direction of arrow A to decrease the angle of the handle portion with respect to the elongate portion. The handle portion 250 may move with respect to the elongate portion 210 in the direction of arrow B to increase the angle (cause the device to become more linear) of the handle portion with respect to the elongate portion.

As best illustrated in FIG. 7, the handle portion 250 may be locked or retained in place with respect to the elongate member 210. The insertion device includes a ratchet member 270. The ratchet member 270 is configured to help retain the handle portion 250 in place with respect to the elongate member 210. The ratchet member 270 includes a first portion 272 that is coupled to the elongate portion 210. The ratchet member 270 also includes a second portion 274 that is coupled to the handle portion 210. The first portion 272 and the second portion 274 are configured to move with respect to each other. Specifically, the first portion 272 and the second portion 274 are configured to move with respect to each other as the handle portion 250 is rotated or pivoted with respect to the elongate portion 210 about axis X (going into the page). In some embodiments, the ratchet member is a member that provides a frictional fit between the first portion 272 and the second portion 274. In such an embodiment, the first portion 272 may be move with respect to the second portion 274 and the ratchet member helps retain the position of the first portion 272 with respect to the second portion 274.

In the illustrated embodiment, the first portion 272 of the ratchet member 270 includes a set or a plurality of teeth members 273. The second portion 274 of the ratchet member 270 includes a set or a plurality of teeth members 275. The teeth members 273 are configured to engage the teeth members 275 to help lock or help retain the handle member 250 in place with respect to the elongate member 210.

The elongate portion 210 defines a lumen 212. The elongate portion 210 includes a sidewall or sidewall member 214 that defines the lumen 212. In some embodiments, the lumen 212 extends along or parallel to at least a portion of a longitudinal axis of the elongate portion 210. In the illustrated embodiment, the sidewall 214 defines a slot or opening 216 that extends along at least a portion of the length of the elongate member 210. The slot or opening 216 is configured to allow the suture of the implant to be removed from the insertion device (for example, by sliding or move out of the slot or opening 216 defined by the sidewall 214).

In the illustrated embodiment, the insertion device 200 includes a plunger 240. The plunger 240 is configured to be disposed within and move within the lumen 212. The plunger 240 is configured to move (for example, slide) from a first location within the lumen 212 to a second location within the lumen 212. The plunger 240 is configured to engage a needle (such as a Keith needle) to move the needle within the lumen 212 or to force the needle from a location within the lumen 212 to a location outside of the lumen 212.

In the illustrated embodiment, the insertion device 200 includes an actuator 280. The actuator 280 may be operatively coupled to the plunger 240. Manipulation or actuation of the actuator 280 can cause the plunger 240 to move within the lumen 212. The actuator 280 may be movably coupled to the handle portion 250 of the insertion device 200. In the illustrated embodiment, the actuator 280 is slidably coupled or configured to be moved or slid along the handle member 250 in the direction of arrow C and in a direction opposite to that of arrow C.

In the illustrated embodiment, the actuator 280 includes a projection portion or projection member 282. The projection member 282 extends above an outer surface of the handle portion 250 to facilitate the access and movement of the actuator 280 with respect to the handle portion 250.

In the illustrated embodiment, the elongate member 210 includes markings 218. The markings 218 are arranged along the length of the elongate member 210. The markings 218 are configured to help indicate to the physician how far into the body of the patient the elongate member has been inserted. For example, in some embodiments, the markings may include a number indicator or may be equally spaced from each other.

In some embodiments, the insertion device 200 is formed or made of molded pieces. In some embodiments, the molded pieces are made of a plastic or a polymer or other biocompatible material. In some embodiments, the insertion device 200 may be disposed of after being used on a single patient.

In some cases, the needle 290 (e.g., a Keith needle), a suture 292 and the penile prosthesis 294 (or other bodily implant) can be used in conjunction with the device 200, or other insertion devices, such as those disclosed herein, for implanting the penile prosthesis (or other bodily implant) into a body of a patient.

For example, in some cases a penile prosthesis may be inserted into a body of the patient using the insertion device 200. Specifically, a cylindrical (e.g., inflatable, malleable, etc.) penile prosthesis can be implanted (inserted, etc.) in a corpus cavernosum of a patient. A method of insertion can include making a penoscrotal or an infrapubic incision in a body of a patient, wherein the incision is located such that a corpus cavernosum of the patient's penis is accessible through the incision. In some cases, an appropriate penile prosthesis can be selected. The selected prosthesis can be attached (coupled with, affixed to, etc.) the suture. The suture 292 can be threaded into (inserted through) an eye of a needle 290, such as the Keith needle. The needle 290 can then be inserted into the lumen 212 of the elongate member 210.

The method includes manipulating the insertion device 200, via the handle 250, to perform a first insertion of the elongate member or portion 210 of the insertion device 200 into the corpus cavernosum, the insertion of the elongate member 210 being made via the incision. The needle can then be expelled from the lumen 212 using the plunger 240 (such as by manipulating the actuation member 280 to move the plunger 240 and also move the needle within the lumen 212 or to a location outside of the lumen 212). In some cases, the actuation of the plunger 240 causes the needle to, at least partially, exit the patient's body via a glans of the patient's penis. The elongate member 210 can again be removed (withdrawn, etc.) from the corpus cavernosum of the patient, leaving the needle 290 and the suture 292 in place (e.g., with the needle partially extending out of the glans and the suture extending from an eye of the needle 290 within the corpus cavernosum to the penile prosthesis being implanted). The penile prosthesis 294 can be implanted into the corpus cavernosum of the patient by drawing the prosthesis through the incision and into to the corpus cavernosum by pulling the needle 290 and the suture 292 through (out of, etc.) the glans of the patient's penis.

After completing implantation of the penile prosthesis, the insertion tool 200 can be disposed of.

FIGS. 8-11 illustrate an insertion device 1200 according to an embodiment.

As illustrated the insertion device 1200 includes an elongate member or portion 1210 and a handle member or portion 1250. The handle portion 1250 is movably coupled to the elongate portion 1210. For example, the handle portion 1250 is rotatably or pivotally coupled to the elongate portion 1210. The handle portion 1250 may move with respect to the elongate portion 1210 to decrease the angle of the handle portion with respect to the elongate portion. The handle portion 1250 may move with respect to the elongate portion 1210 to increase the angle (cause the device to become more linear) of the handle portion with respect to the elongate portion.

The handle portion 1250 may be locked or retained in place with respect to the elongate member 1210. The insertion device includes a ratchet member or lock member 1270. The ratchet member 1270 is configured to help retain the handle portion 1250 in place with respect to the elongate member 1210.

In the illustrated embodiment, the handle portion 1250 includes a first member 1250A and a second member 1250B. The first member 1250A of the handle portion 1250 may be snap coupled, glued, or coupled to the second member 1250B of the handle portion 1250 via any other coupling means or method.

In the illustrated embodiment, the elongate member 1210 includes a first member 1210A and a second member 1210B. The first member 1210A may be snap coupled, glued, or coupled to the second member 1210B of the elongate member 1210 via any other coupling means or method.

The ratchet member or lock member 1270 is disposed between the first member 1210A of the elongate member 1210 and the second member 1210B of the elongate member 1210. The ratchet member or lock member 1270 includes a set or series of teeth or engagement members 1272. The first member 1210A of the elongate member 1210 also includes a set or series of teeth or engagement members 1212. The teeth or engagement members 1272 of the ratchet or lock member 1270 are configured to engage the teeth or engagement members 1212 of the first member 1210A.

The ratchet member or lock member 1270 is biased towards the first member 1210A. Specifically, the ratchet member or lock member 1270 is biased towards to the first member 1210A such that the teeth or engagement members 1272 of the ratchet member or lock member 1270 engage the teeth or engagement members 1212 of the first member 1210A to lock or retain the elongate member 1210 in place or position with respect to the handle portion 1250. In the illustrated embodiment, a spring 1273 is disposed between the first member 1210A and the second member 1210B and is configured to engage the ratchet member or lock member 1270 to bias the ratchet member or lock member 1270 towards the first member 1210A.

To move or rotate the elongate member 1210 with respect to the handle portion 1250, the ratchet member or lock member 1270 may be pressed or moved away from the first member 1210A of the elongate member 1210 to disengage the teeth or engagement members 1272 from the teeth or engagement members 1212. The elongate member 1210 may then be moved with respect to the handle member 1250. The ratchet member or lock member 1270 may be released and allowed to move back towards the first member 1210A of the elongate member 1210 to lock the elongate member 1210 in place with respect to the handle member 1250.

In the illustrated embodiment, the insertion device 1200 includes a plunger 1240. The plunger 1240 is configured to be disposed within and move within a lumen 1213. The plunger 1240 is configured to move (for example, slide) from a first location within the lumen 1213 to a second location within the lumen 1213. The plunger 1240 is configured to engage a needle (such as a Keith needle) to move the needle within the lumen 1213 or to force the needle from a location within the lumen 1213 to a location outside of the lumen 1213.

In the illustrated embodiment, the insertion device 1200 includes an actuator 1280. The actuator 1280 may be operatively coupled to the plunger 1240. Manipulation or actuation of the actuator 1280 can cause the plunger 1240 to move within the lumen 1213. The actuator 1280 may be movably coupled to the handle portion 1250 of the insertion device 1200.

In the illustrated embodiment, the elongate member 1210 includes markings 1218. The markings 1218 are arranged along the length of the elongate member 1210. The markings 1218 are configured to help indicate to the physician how far into the body of the patient the elongate member has been inserted. For example, in some embodiments, the markings may include a number indicator or may be equally spaced from each other.

In some embodiments, the insertion device 1200 is formed or made of molded pieces. In some embodiments, the molded pieces are made of a plastic or a polymer or other biocompatible material. In some embodiments, the insertion device 1200 may be disposed of after being used on a single patient.

In some cases, the needle (e.g., a Keith needle), a suture, and the penile prosthesis (or other bodily implant) can be used in conjunction with the device 1200, or other insertion devices, such as those disclosed herein, for implanting the penile prosthesis (or other bodily implant) into a body of a patient.

Figure 12:
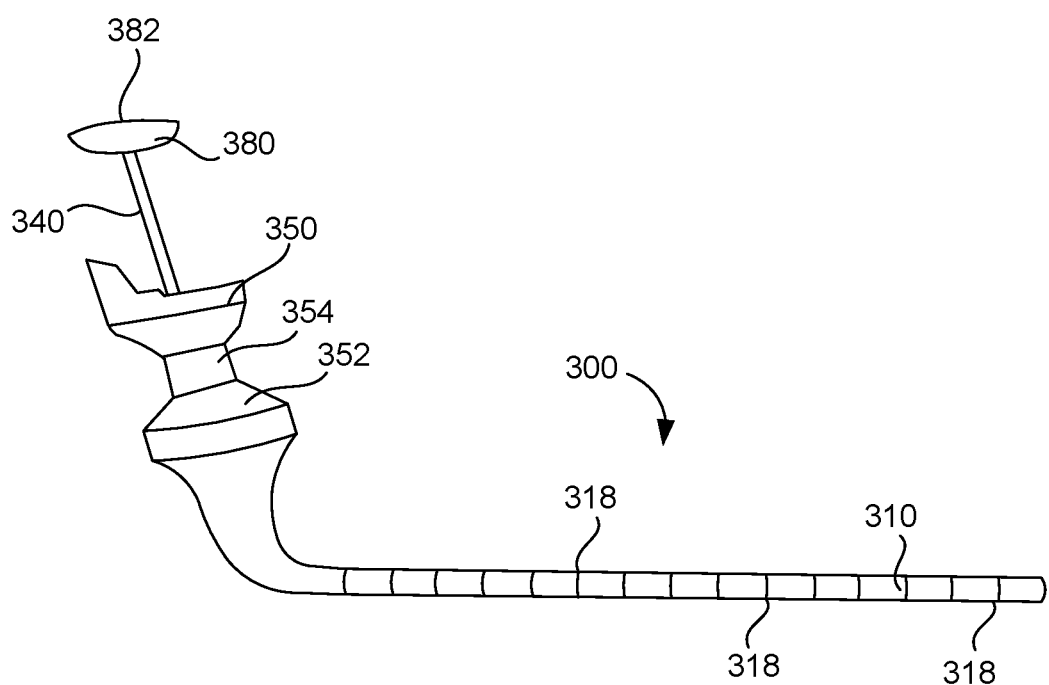
FIG. 12 is a side view of an insertion device according to an embodiment.
Figure 13:
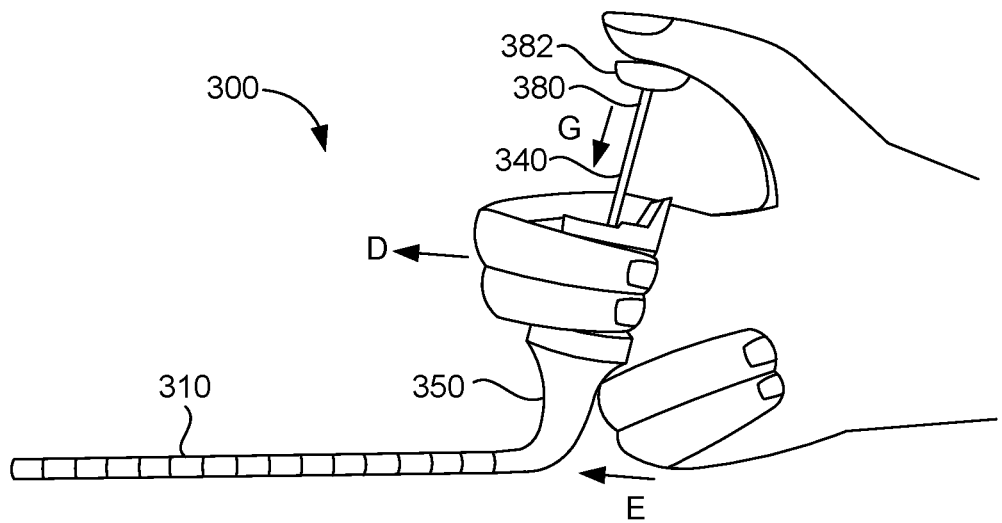
FIGS. 13 and 14 are side views of the insertion device of FIG. 12.
Figure 14:
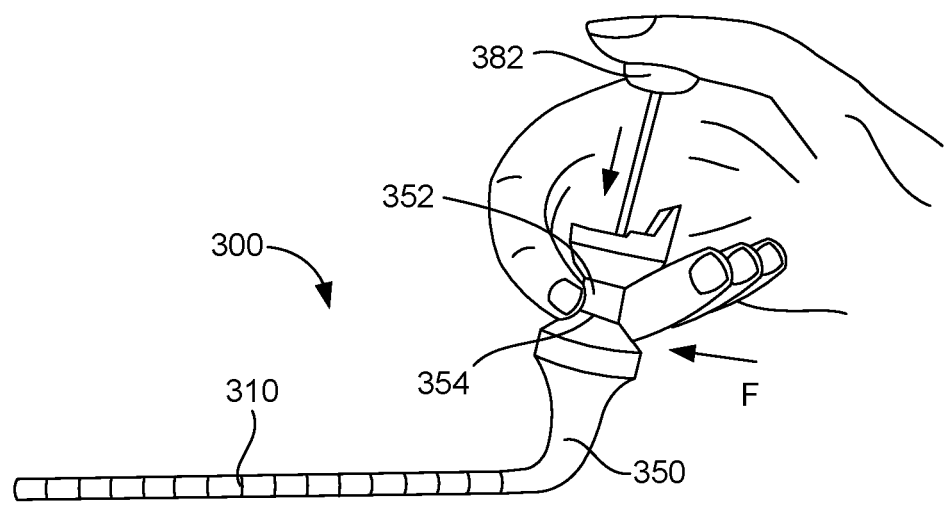
Figure 15:
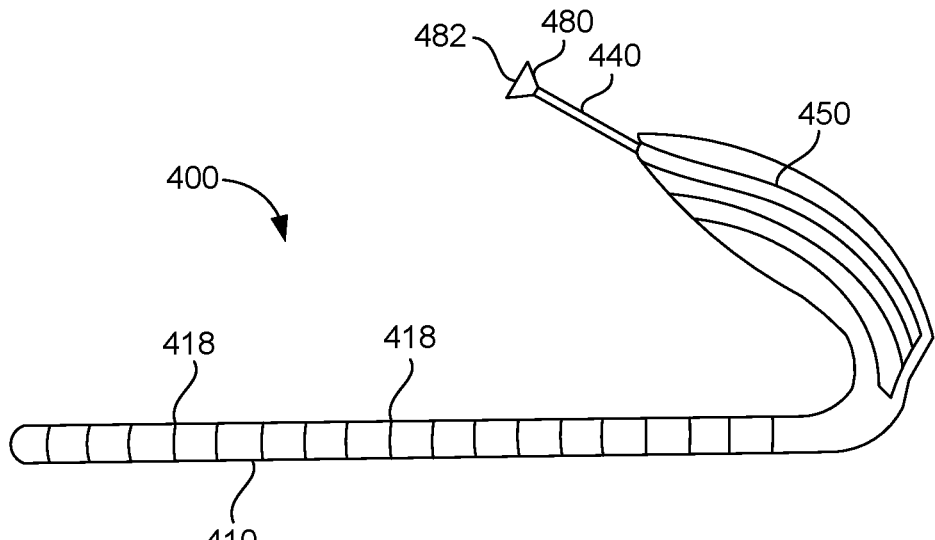
FIG. 15 is a side view of an insertion device according to an embodiment.
Figure 16:
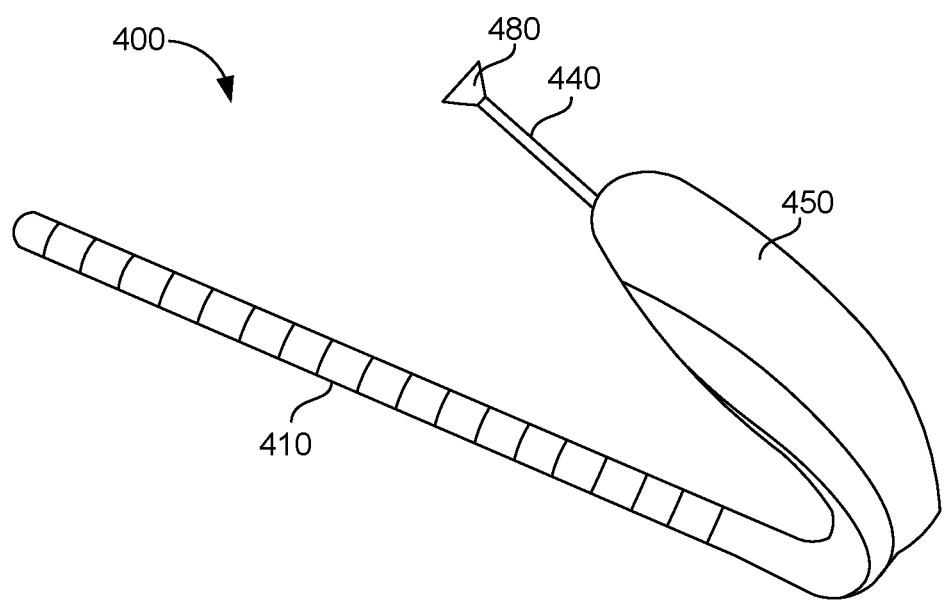
FIG. 16 is a perspective view of the insertion device of FIG. 15.
Figure 17:
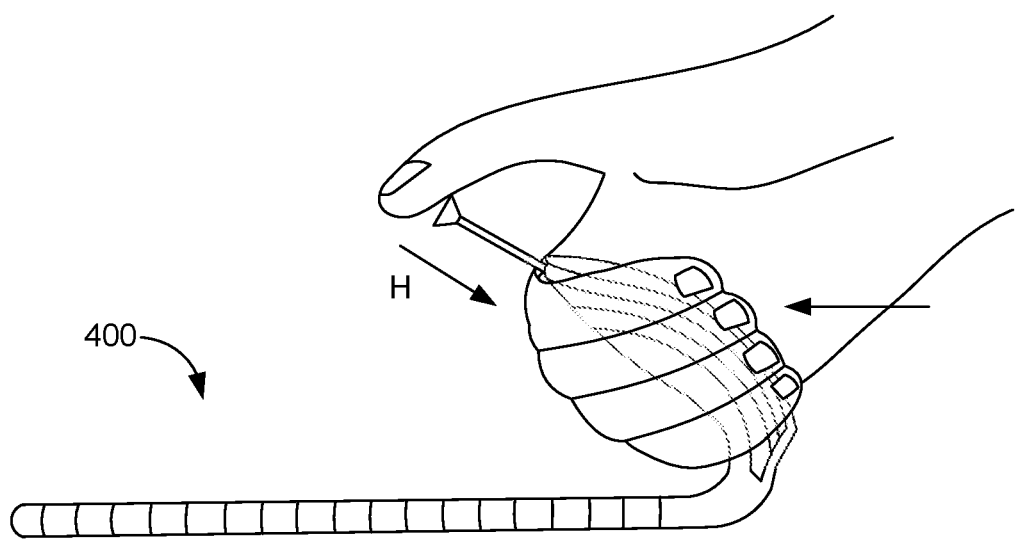
FIG. 17 is a side view of the insertion device of FIG. 15.
Figure 18:
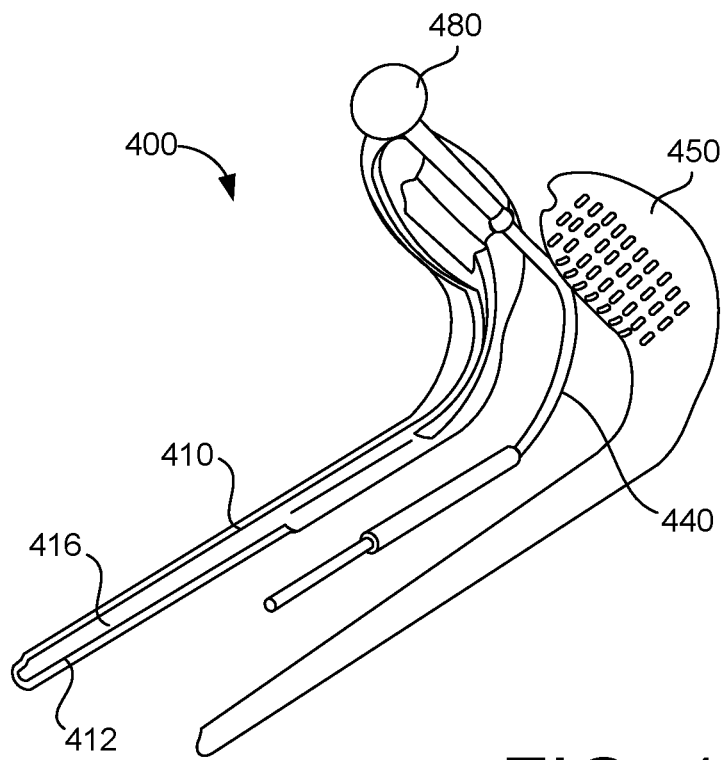
FIG. 18 is an exploded view of the insertion device of FIG. 15.

FIGS. 12-14 illustrate an insertion device 300 according to an embodiment. As illustrated, the insertion device 300 includes an elongate member or portion 310 and a handle member or portion 350. The handle portion 350 includes a grip portion 352. The grip portion is configured to allow the physician to grasp or grip the device with a single hand. The grip portion 352 includes a trough or depression 354 that allows the device to be gripped with a single hand. FIG. 13 illustrates the device 300 being gripped in a first manor and FIG. 14 illustrates the device 300 being gripped in a second manor. As illustrated in FIG. 13, force may be applied at arrows D and E to insert the device 300 into the body of the patient. As illustrated in FIG. 14, force may be applied at arrow F to insert the device 300 into the body of the patient. In some embodiments, the insertion device 300 may be inserted and actuated by the physician with a single hand and may help minimize the contact with the body of the patient.

The elongate portion 310 defines a lumen (not illustrated). The elongate portion 310 includes a sidewall or sidewall member 314 that defines the lumen. In some embodiments, the lumen extends along or parallel to at least a portion of a longitudinal axis of the elongate portion 310. In the illustrated embodiment, the sidewall 314 defines a slot or opening that extends along at least a portion of the length of the elongate member 310. The slot or opening is configured to allow the suture of the implant to be removed from the insertion device 300 (for example, by sliding or move out of the slot or opening defined by the sidewall 314).

In the illustrated embodiment, the insertion device 300 includes a plunger 340. The plunger 340 is configured to be disposed within and move within the lumen. The plunger 340 is configured to move (for example, slide) from a first location within the lumen to a second location within the lumen. The plunger 340 is configured to engage a needle (such as a Keith needle) to move the needle within the lumen or to force the needle from a location within the lumen to a location outside of the lumen.

In the illustrated embodiment, the insertion device 300 includes an actuator 380. The actuator 380 may be operatively coupled to the plunger 340. Manipulation or actuation of the actuator 380 can cause the plunger 340 to move within the lumen. In the illustrated embodiment, the actuator 380 may be moved in the direction of arrow G to cause the plunger 340 to move within the lumen.

In the illustrated embodiment, the elongate member 310 includes markings 318. The markings 318 are arranged along the length of the elongate member 310. The markings 318 are configured to help indicate to the physician how far into the body of the patient the elongate member 300 has been inserted. For example, in some embodiments, the markings 318 may include a number indicator or may be equally spaced from each other.

In some embodiments, the insertion device 300 is formed or made of molded pieces. In some embodiments, the molded pieces are made of a plastic or a polymer or other biocompatible material. In some embodiments, the insertion device 300 may be disposed of after being used on a single patient.

FIGS. 15-18 illustrate an insertion device 400 according to an embodiment. As illustrated, the insertion device 400 includes an elongate member or portion 410 and a handle member or portion 450. The handle portion 450 is disposed at an angle with respect to the elongate member 410. In the illustrated embodiment, the handle portion 450 is disposed at an acute angle with respect to the elongate member 410. In some embodiments, orientation or position of the handle portion 450 with respect to the elongate member 410 allows for the device 400 to be used in small spaces.

The elongate portion 410 defines a lumen 412. The elongate portion 410 includes a sidewall or sidewall member 414 that defines the lumen 412. In some embodiments, the lumen 412 extends along or parallel to at least a portion of a longitudinal axis of the elongate portion 410. In the illustrated embodiment, the sidewall 414 defines a slot or opening 416 that extends along at least a portion of the length of the elongate member 410. The slot or opening 416 is configured to allow the suture of the implant to be removed from the insertion device 400 (for example, by sliding or move out of the slot or opening defined by the sidewall 414).

In the illustrated embodiment, the insertion device 400 includes a plunger 440. The plunger 440 is configured to be disposed within and move within the lumen 412. The plunger 440 is configured to move (for example, slide) from a first location within the lumen 412 to a second location within the lumen 412. The plunger 440 is configured to engage a needle (such as a Keith needle) to move the needle within the lumen 412 or to force the needle from a location within the lumen 412 to a location outside of the lumen 412.

In the illustrated embodiment, the insertion device 400 includes an actuator 480. The actuator 480 may be operatively coupled to the plunger 440. Manipulation or actuation of the actuator 480 can cause the plunger 440 to move within the lumen 412. In the illustrated embodiment, the actuator 480 may be moved in the direction of arrow H to cause the plunger 440 to move within the lumen 412.

In the illustrated embodiment, the elongate member 410 includes markings 418. The markings 418 are arranged along the length of the elongate member 410. The markings 418 are configured to help indicate to the physician how far into the body of the patient the elongate member 400 has been inserted. For example, in some embodiments, the markings 418 may include a number indicator or may be equally spaced from each other.

In some embodiments, the insertion device 400 is formed or made of molded pieces. In some embodiments, the molded pieces are made of a plastic or a polymer or other biocompatible material. In some embodiments, the insertion device 400 may be disposed of after being used on a single patient.

Figure 19:
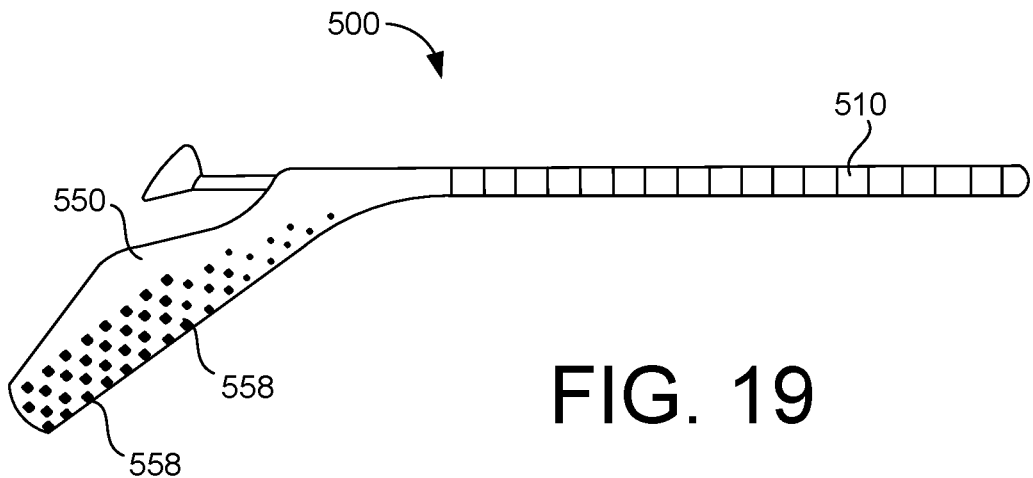
FIG. 19 is a side view of an insertion device according to an embodiment.

FIG. 19 illustrates an insertion device 500 according to an embodiment. As illustrated, the insertion device 500 includes an elongate member or portion 510 and a handle member or portion 550. The handle portion 550 is disposed at an angle with respect to the elongate member 510. The handle portion 550 provides for a pistol type grip and includes grip members or grip ridges 558.

Figure 20:
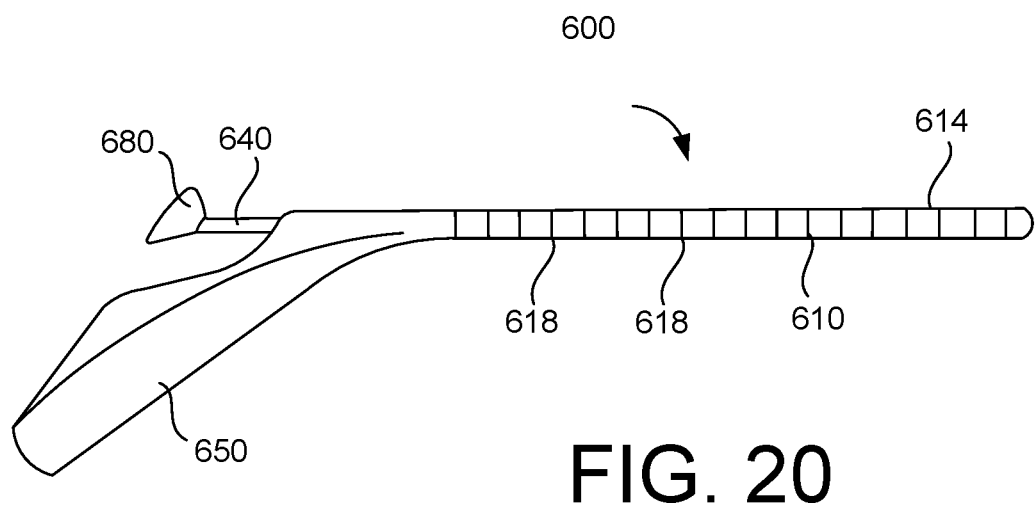
FIG. 20 is a side view of an insertion device according to an embodiment.
Figure 21:
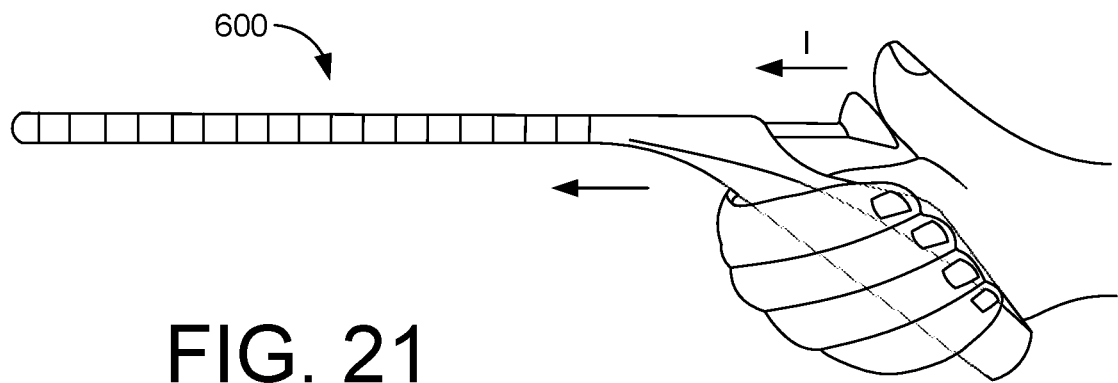
FIG. 21 is a side view of the insertion device of FIG. 20.

FIGS. 20-21 illustrate an insertion device 600 according to an embodiment. As illustrated, the insertion device 600 includes an elongate member or portion 610 and a handle member or portion 650. The handle portion 650 is disposed at an angle with respect to the elongate member 610. The handle portion 650 provides for a pistol type grip.

The elongate portion 610 defines a lumen. The elongate portion 610 includes a sidewall or sidewall member 614 that defines the lumen. In some embodiments, the lumen extends along or parallel to at least a portion of a longitudinal axis of the elongate portion 610. In the illustrated embodiment, the sidewall 614 defines a slot or opening that extends along at least a portion of the length of the elongate member 610. The slot or opening is configured to allow the suture of the implant to be removed from the insertion device 600 (for example, by sliding or move out of the slot or opening defined by the sidewall 614).

In the illustrated embodiment, the insertion device 600 includes a plunger 640. The plunger 640 is configured to be disposed within and move within the lumen. The plunger 640 is configured to move (for example, slide) from a first location within the lumen to a second location within the lumen. The plunger 640 is configured to engage a needle (such as a Keith needle) to move the needle within the lumen or to force the needle from a location within the lumen to a location outside of the lumen.

In the illustrated embodiment, the insertion device 600 includes an actuator 680. The actuator 680 may be operatively coupled to the plunger 640. Manipulation or actuation of the actuator 680 can cause the plunger 640 to move within the lumen. In the illustrated embodiment, the actuator 680 may be moved in the direction of arrow I to cause the plunger 640 to move within the lumen.

In the illustrated embodiment, the elongate member 610 includes markings 618. The markings 618 are arranged along the length of the elongate member 610. The markings 618 are configured to help indicate to the physician how far into the body of the patient the elongate member 600 has been inserted. For example, in some embodiments, the markings 618 may include a number indicator or may be equally spaced from each other.

In some embodiments, the insertion device 600 is formed or made of molded pieces. In some embodiments, the molded pieces are made of a plastic or a polymer or other biocompatible material. In some embodiments, the insertion device 400 may be disposed of after being used on a single patient.

Figure 22:
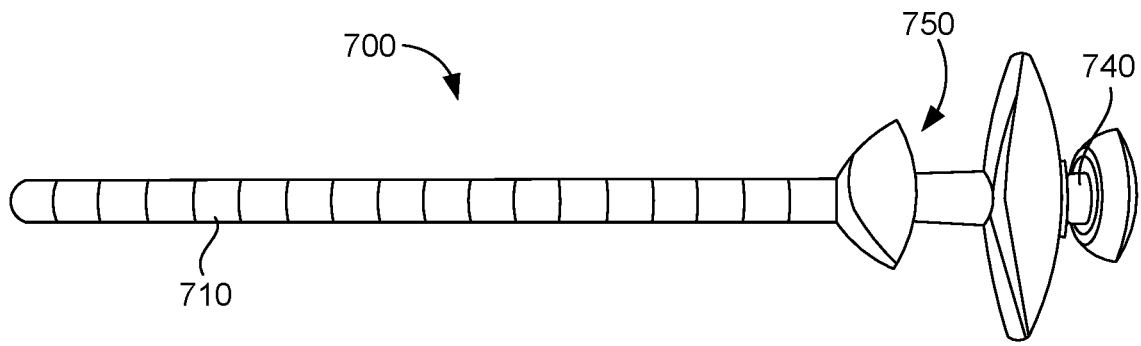
FIG. 22 is a side view of an insertion device according to an embodiment.

FIG. 22 illustrates an insertion device 700 according to an embodiment. As illustrated, the insertion device 700 includes an elongate member or portion 710 and a handle member or portion 750.

In the illustrated embodiment, the insertion device 700 includes a plunger 740. The plunger 740 is configured to be disposed within and move within the lumen. The plunger 740 is configured to move (for example, slide) from a first location within the lumen to a second location within the lumen. The plunger 740 is configured to engage a needle (such as a Keith needle) to move the needle within the lumen or to force the needle from a location within the lumen to a location outside of the lumen.

Figure 23:
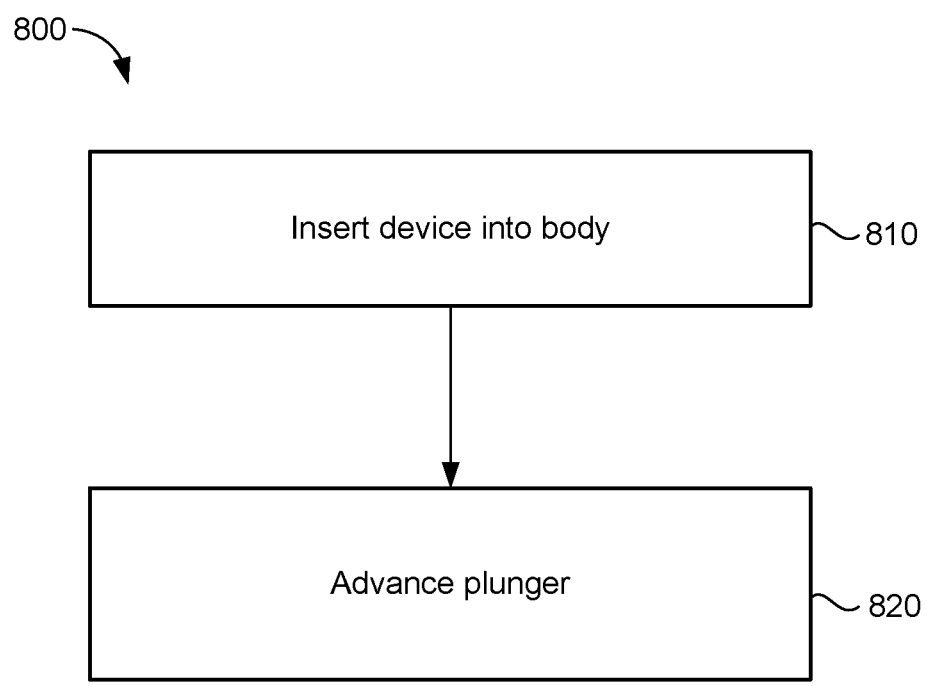
FIG. 23 is a flow chart of a method according to an embodiment.

FIG. 23 is a flow chart for a method 800 according to an embodiment. The method 800 includes at 810 inserting a medical device into a body of a patient. At 820, advancing a plunger. In some embodiments, the advancing the plunger includes expelling a needle from the medical device. In some embodiments, the method 800 includes moving (such as pivoting or rotating) a handle portion of the medical device with respect to an elongate portion of the medical device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An insertion device, comprising:
an elongate member defining a lumen;
a handle member pivotally coupled to the elongate member;
a plunger member, at least a portion of the plunger member being disposed within the lumen defined by the elongate member;
an actuation member operatively coupled to the plunger member, the plunger member being configured to move from a first position within the lumen to a second location within the lumen in response to the actuation member being actuated; and
a ratchet member, the ratchet member having a first portion coupled to the elongate member and a second portion coupled to the handle member, the first portion of the ratchet member being configured to move with respect to the second portion of the ratchet member, the first portion of the ratchet member having a plurality of teeth members, the second portion of the ratchet member having a plurality of teeth members, the plurality of teeth members of the first portion of the ratchet member being configured to engage the plurality of teeth members of the second portion of the ratchet member.

2. The insertion device of claim 1,
wherein the ratchet member being configured to help retain the handle member in a first position with respect to the elongate member.

3. The insertion device of claim 1,
wherein the ratchet member being configured to help retain the handle member in a first position with respect to the elongate member, the ratchet member being configured to help retain the handle member in a second position with respect to the elongate member, the first position being different than the second position.

4. The insertion device of claim 1, wherein the actuation member is movably coupled to the handle member.

5. The insertion device of claim 1, wherein the actuation member is slideably coupled to the handle member.

6. The insertion device of claim 1, wherein the actuation member includes an extension member that extends from an outer surface of the handle member.

7. The insertion device of claim 1, wherein the plunger is configured to engage a needle and move the needle from a first location within the lumen defined by the elongate member to a second location within the lumen defined by the elongate member.

8. The insertion device of claim 1, wherein the plunger is configured to engage a needle and move the needle from a location within the lumen defined by the elongate member to a location outside of the lumen defined by the elongate member.

9. The insertion device of claim 1, wherein the elongate member includes a sidewall that defines the lumen, the sidewall includes a slot that extends along at least a portion of a length of the elongate member.

10. The insertion device of claim 1, wherein the elongate member incudes a plurality of markings along a length of the elongate member.

11. A medical device, comprising:
an insertion device, having,
an elongate member defining a lumen;
a handle member pivotally coupled to the elongate member;
a plunger member, at least a portion of the plunger member being disposed within the lumen defined by the elongate member; and
an actuation member operatively coupled to the plunger member, the plunger member being configured to move from a first position within the lumen to a second location within the lumen in response to the actuation member being actuated;
an implant, having an inflation member;
a needle, the needle coupled to the inflation member, the needle configured to be disposed at least partially within the lumen defined by the elongate member; and
a ratchet member, the ratchet member having a first portion coupled to the elongate member and a second portion coupled to the handle member, the first portion of the ratchet member configured to move with respect to the second portion of the ratchet member.

\* \* \* \* \*